(12) United States Patent
DeGeorge et al.

(10) Patent No.: US 8,556,992 B2
(45) Date of Patent: Oct. 15, 2013

(54) COMPOSITIONS AND METHODS FOR LIGHTENING THE COLOR OF RELAXED OR STRAIGHTENED HAIR

(75) Inventors: Michael DeGeorge, Middletown, NJ (US); Jeremy Puco, Budd Lake, NJ (US)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 13/695,482

(22) PCT Filed: Mar. 30, 2011

(86) PCT No.: PCT/US2011/030528
§ 371 (c)(1),
(2), (4) Date: Oct. 31, 2012

(87) PCT Pub. No.: WO2011/139433
PCT Pub. Date: Nov. 10, 2011

(65) Prior Publication Data
US 2013/0042883 A1 Feb. 21, 2013

Related U.S. Application Data

(60) Provisional application No. 61/329,600, filed on Apr. 30, 2010.

(51) Int. Cl.
*D06L 3/02* (2006.01)
*A61K 8/00* (2006.01)

(52) U.S. Cl.
USPC .................................. 8/110; 8/111; 424/70.1

(58) Field of Classification Search
USPC ....................................... 8/110, 111; 424/70.1
See application file for complete search history.

(56) References Cited

U.S. PATENT DOCUMENTS

| 6,613,311 B2 * | 9/2003 | Imperial ........................ 424/62 |
| 2002/0141954 A1 | 10/2002 | Imperial |
| 2003/0086882 A1 | 5/2003 | Schmenger et al. |
| 2003/0190297 A1 | 10/2003 | Narasimhan et al. |
| 2005/0193501 A1 | 9/2005 | Chan et al. |

OTHER PUBLICATIONS

International Search Report for Application No. PCT/US2011/030528, dated Dec. 26, 2011 (2 pages).
PCT/IB/308 Form for Application No. PCT/US2011/030528.

* cited by examiner

*Primary Examiner* — Eisa Elhilo
(74) *Attorney, Agent, or Firm* — O'Brien Jones, PLLC.

(57) ABSTRACT

Disclosed are methods and compositions of lightening the color of hair that has been recently contacted with a relaxing or straightening composition, the method comprising combining a bleach composition comprising at least one oxidizing agent selected from the group consisting of persulfates, perborates, percarbonates, their salts and mixtures thereof, and at least one rheology-modifying agent, with a developer composition comprising hydrogen peroxide and a cosmetically acceptable carrier in order to form a lightening composition, wherein the pH of the lightening composition is from about 2 to about 7; applying the lightening composition onto the hair; leaving the lightening composition on the hair for a time period sufficient to achieve an increase of 1 to 4 in the tone height of the hair; and rinsing the hair with water.

19 Claims, No Drawings

COMPOSITIONS AND METHODS FOR LIGHTENING THE COLOR OF RELAXED OR STRAIGHTENED HAIR

CROSS-REFERENCE TO RELATED APPLICATION

This is a national stage application of PCT/US2011/030528, filed internationally on Mar. 30, 2011, which claims priority to U.S. Provisional Application No. 61/329,600 filed on Apr. 30, 2010.

BACKGROUND OF THE INVENTION

Chemical treatments on human hair such as relaxers, straighteners, waves, perms, oxidative and direct dyes, highlights and bleaches are known to result in hair breakage and loss, dryness, roughness and brittleness, and skin and/or scalp irritation. Such chemical treatments employ various reducing and oxidizing agents, alkalizing agents, and coloring agents that help re-shape, artificially color or decolorize hair. Often times, these treatments are used with the application of heat and mechanical combing or brushing, which may contribute to more damage to the hair. Thus, conventional and customary practice by consumers and hair dressers is to have a waiting period of at least 24 hours, preferably, a few days, in between two different chemical hair treatments in order to prevent or reduce irritation to the skin or scalp and the potential damage to hair caused by different chemical treatments within a short period of time, i.e., a few hours. Moreover, a waiting period of at least 24 hours is generally recommended in order to reduce the chance of having a reaction between different chemical treatments, for example, straightening, then bleaching the hair, resulting in an undesirable hair shade.

One of the problems with hair straightening and relaxing methods is that they may prevent the hair from being dyed or bleached correctly in order to achieve the desired shade or lightening effects, especially when the coloration or bleaching step is conducted immediately after the straightening or relaxing steps. Another problem is that when hair straightening or relaxing is immediately followed by a conventional oxidative hair color that employs hydrogen peroxide as the only and/or primary oxidizing agent, the combined use of peroxide with the other ingredients in the hair straighteners and relaxers can result in significant decrease in the quality of the hair fibers, leading to increased roughness and damage to the hair.

It has now been surprisingly discovered that recently chemically straightened or relaxed hair can be lightened in color by combining a bleach composition comprising at least one oxidizing agent selected from the group consisting of persulfates, perborates, percarbonates, their salts and mixtures thereof, and at least one rheology-modifying agent, with a developer composition comprising hydrogen peroxide and a cosmetically acceptable carrier, in order to form a lightening composition, wherein the pH of the lightening composition is from about 2 to about 7, and applying the lightening composition onto the straightened or relaxed hair.

The degree of lightening of the hair may be expressed in terms of "tone" based on the classification of natural shades, one tone separating each shade from that which immediately follows or precedes it. The tone levels are graded from 1 to 10, one unit corresponding to one tone wherein the higher the tone number, the lighter the shade.

It has also now been surprisingly discovered that lightening of the color of hair can be achieved using the methods and compositions of the present invention, and particularly, using a composition having a pH of from 2 to 7. Also, it has been surprisingly discovered that the color of hair that has been recently straightened or relaxed by an alkali-based composition can be lightened using the compositions and method of the present invention. Moreover, it was surprisingly discovered that by using the inventive system, it was possible to achieve acceptable degrees of lightening of the color of the hair that corresponds to an increase in color tone height of up to 4.

The present invention also provides a way to neutralize the hair after it has been treated with a relaxer or straightening composition without having to use a conventional neutralizing composition after such treatment. The method and compositions of the present invention also provide a way to correct the undesirable noticeable greenish yellow to yellowish brown tinge to the hair that results from straightening or relaxing, especially when one has naturally gray hair. At the same time, the use of the present invention reduces the chance of degradation of hair keratin, thus decreasing the chance of hair breakage and loss and allowing the hair to retain a desirable softness and shape.

BRIEF SUMMARY OF THE INVENTION

The present invention is directed to a method of lightening the color of hair that has been recently contacted with a relaxing or straightening composition, the method comprising:
(a) combining a bleach composition comprising at least one oxidizing agent selected from the group consisting of persulfates, perborates, percarbonates, their salts and mixtures thereof; and at least one rheology-modifying agent, with a developer composition comprising hydrogen peroxide and a cosmetically acceptable carrier in order to form a lightening composition, wherein the pH of the lightening composition is from about 2 to about 7;
(b) applying the lightening composition onto the hair that has been recently contacted with a relaxing or straightening composition;
(c) leaving the lightening composition on the hair for a time period sufficient to achieve an increase of 1 to 4 in the tone height of the hair; and
(d) rinsing the hair with water.

The present invention is directed to a composition for lightening the color of hair that has been recently contacted with a relaxing or straightening composition, the composition comprising:
(a) a bleach composition containing:
　i. at least one oxidizing agent selected from the group consisting of persulfates, perborates, percarbonates, their salts and mixtures thereof; and
　ii. at least one rheology-modifying agent; and
(b) a developer composition containing:
　i. hydrogen peroxide; and
　ii. a cosmetically acceptable carrier; and
wherein the lightening composition has a pH of about 2 to about 7.

According to a preferred embodiment, the lightening composition is prepared by combining the bleach composition and the developer composition and is then applied to hair that has been recently contacted with a relaxing or straightening composition in order to simultaneously lighten the color of the hair and neutralize any excess relaxing or straightening composition on the hair.

DETAILED DESCRIPTION OF THE INVENTION

Other than in the operating examples, or where otherwise indicated, all numbers expressing quantities of ingredients or reaction conditions are to be understood as being modified in all instances by the term "about".

As used herein, the expression "at least one" means one or more and thus includes individual components as well as mixtures/combinations.

As used herein, the expression "chemically altering" means contacting the hair with at least one composition containing at least one chemical ingredient that changes or contributes to changing the shape and/or the color of the hair.

As used herein, the term "applying" means contacting the hair with at least one of the compositions of the invention.

As used herein, the terms "straightening" or "straighten" or "relaxing" or "relax" the hair mean to remove the curl from the hair or reduce the degree of curl of the hair. It also means changing the shape of hair or the degree of curl in the hair to make the hair more straight.

As used herein, "cosmetically acceptable" means that the item in question is compatible with any human keratin material and in particular human keratinous fibers, such as human hair.

As used herein, "cosmetically acceptable carrier" means a carrier that is compatible with any human keratin material and in particular human keratinous fibers, such as human hair.

As used herein, "recently contacted" means that the time period between contacting the hair with a relaxing or straightening composition and lightening the color of the hair using the compositions and methods of the present invention is not more than twenty four hours.

As used herein, "natural hair color" refers to the color of hair resulting from the melanin pigments present in the hair.

As used herein, "conditioning" means imparting to at least one keratinous fiber at least one property chosen from combability, manageability, moisture-retentivity, luster, shine, and softness. In case of combing, the level of conditioning is evaluated by measuring, and comparing, the ease of combability of the treated hair and of the untreated hair in terms of combing work (gm-in).

As used herein, "formed from," means obtained from chemical reaction of, wherein "chemical reaction," includes spontaneous chemical reactions and induced chemical reactions. As used herein, the phrase "formed from", is open ended and does not limit the components of the composition to those listed.

As used herein, the term "rheology-modifying agent" or "rheology modifier" means any compound capable of giving a viscosity to the oxidizing composition such that, once it is applied onto keratin fibres, this composition does not run, and remains perfectly localized at the point of application.

Composition Having a pH Value of not Greater than 7

The lightening composition of the present invention, having a pH value of not greater than 7, is formed by combining the bleach composition and the developer composition of the present invention. After it is formed, the lightening composition is then applied onto hair that has been recently contacted with a relaxing or straightening composition in order to lighten the color of the hair. In addition, the lightening composition serves to neutralize excess alkaline material remaining from the chemical relaxing or straightening treatment to avoid and minimize damage and/or irritation to the hair protein or skin while lightening the hair. The lightening composition of the present invention may also be called a "neutralizer" or "neutralizing composition," capable of accomplishing the foregoing neutralization of residual alkalinity when it is applied substantially immediately following the treatment of hair with a hair-relaxing or hair-straightening composition.

The lightening composition of the present invention is formed such that it has an acidic pH in the range of from about 2 to about 7, preferably about 2 to about 5.

The lightening composition of the present invention is preferably formed from the combination of a bleach composition comprising at least one oxidizing agent chosen from persulfates, perborates, percarbonates, their salts and mixtures thereof, and at least one rheology-modifying agent and a developer composition comprising hydrogen peroxide and a cosmetically acceptable carrier.

Bleach Composition

The at least one oxidizing agent of the bleach compositions of the present invention includes, but is not limited to, persulfates, perborates, percarbonates, their salts and mixtures thereof.

Preferred persulfates are monopersulfates such as, for example, potassium persulfate, sodium persulfate, ammonium persulfate, as well as mixtures thereof.

The preferred oxidizing agents in the present invention are potassium persulfate, sodium persulfate and mixtures thereof.

The at least one oxidizing agent of the bleach or lightening compositions of the present invention is utilized in these compositions in an amount sufficient to lighten hair.

In general, the at least one oxidizing agent of the bleach composition is present in an amount ranging from 10% by weight to 100% by weight, preferably from about 20% to about 90% by weight, more preferably from about 30% to about 80% by weight, even more preferably from about 40% to about 75% by weight, based on the total weight of the bleach composition.

According to a preferred embodiment, the at least one oxidizing agent of the bleach composition will be present in an amount of at least 40% by weight, based on the total weight of the bleach composition.

The bleach composition of the present invention may use a rheology-modifying agent. The at least one rheology modifying agent that may be used in the present invention includes, but is not limited to, nonionic, anionic, cationic or amphoteric polymers, and other rheology modifiers such as cellulose-based thickeners (hydroxyethylcellulose, hydroxypropylcellulose, carboxymethylcellulose, cationic cellulose ether derivatives, quaternized cellulose derivatives, etc.), guar gum and its derivatives (hydroxypropyl guar, cationic guar derivatives, etc.), gums of microbial origin (xanthan gum, scleroglucan gum, etc.), crosslinked homopolymers of acrylic acid or of acrylamidopropanesulfonic acid and associative polymers as described below.

In particular, the compositions of the present invention may comprise at least one polymer chosen from nonionic, anionic, cationic or amphoteric amphiphilic polymers.

The amphiphilic polymers may contain a hydrophobic chain that is a saturated or unsaturated, aromatic or non-aromatic, linear or branched $C_6$-$C_{30}$ hydrocarbon-based chain, optionally comprising one or more oxyalkylene (oxyethylene and/or oxypropylene) units.

Among the cationic amphiphilic polymers comprising a hydrophobic chain that may be found are cationic polyurethanes or cationic copolymers comprising vinyllactam units and in particular vinylpyrrolidone units.

As examples of nonionic amphiphilic polymers containing a hydrophobic chain, mention may be made, inter alia, of:

(1) celluloses modified with groups comprising at least one saturated or unsaturated, linear or branched $C_6$-$C_{30}$ hydrocarbon-based chain, for instance hydroxyethylcelluloses modified with groups comprising at least one hydrophobic chain as defined previously, such as especially Natrosol Plus Grade 330 CS ($C_{16}$ alkyls—sold by the company Aqualon); Bermocoll EHM 100 (sold by the company Berol Nobel), Amercell Polymer HM-1500 (hydroxyethylcellulose modified with a polyethylene glycol (15) nonylphenyl ether group—sold by the company Amerchol);

(2) hydroxypropyl guars modified with groups comprising at least one hydrophobic chain as defined, for example Jaguar XC-95/3 ($C_{14}$ alkyl chain—sold by the company Rhodia Chimie); Esaflor HM 22 ($C_{22}$ alkyl chain—sold by the company Lamberti); RE210-18 ($C_{14}$ alkyl chain) and RE205-1 ($C_{20}$ alkyl chain) sold by the company Rhodia Chimie;

(3) copolymers of vinylpyrrolidone and of hydrophobic monomers containing a hydrophobic chain as defined above, for instance Antaron or Ganex V216 (vinylpyrrolidone/hexadecene copolymers); Antaron or Ganex V220 (vinylpyrrolidone/eicosene copolymers), sold by the company. I.S.P.;

(4) copolymers of $C_1$-$C_6$ alkyl (meth)acrylates and of amphiphilic monomers containing a hydrophobic chain;

(5) copolymers of hydrophilic (meth)acrylates and of hydrophobic monomers comprising at least one hydrophobic chain, for instance the polyethylene glycol methacrylate/lauryl methacrylate copolymer;

(6) polymers with an aminoplast ether skeleton containing at least one fatty chain, such as the Pure Thix compounds sold by the company Sud-Chemie;

(7) linear (block structure), grafted or starburst polyurethane polyethers comprising in their chain at least one hydrophilic block, which is generally a polyoxyethylene block which may comprise between 50 and 1 000 oxyethylene units approximately, and at least one hydrophobic block, which may comprise aliphatic groups alone, optionally combined with cycloaliphatic and/or aromatic blocks. Preferably, the polyurethane polyethers comprise at least two $C_8$-$C_{30}$ hydrocarbon-based hydrophobic chains, separated by a hydrophilic block; the hydrophobic chains may be pendent chains or chains with one or more of the end groups of the hydrophilic block(s).

The polyurethane polyethers comprise a urethane bond between the hydrophilic blocks, but may also contain hydrophilic blocks linked to the lipophilic blocks via other chemical bonds.

Examples of polyurethane polyethers that may be mentioned include Nuvis FX 1100 (European and US INCI name "Steareth-100/PEG-136/HMDI Copolymer" sold by the company Servo Delden); Rheolate 205, 208, 204 or 212 (sold by the company Rheox); Elfacos T210 ($C_{12}$-$C_{14}$ alkyl chain) and Elfacos T212 ($C_{18}$ alkyl chain) sold by the company Akzo.

The anionic amphiphilic polymers containing a hydrophobic chain that may be used comprise, as hydrophobic chain, at least one saturated or unsaturated, aromatic or non-aromatic, linear or branched $C_8$-$C_{30}$ hydrocarbon-based chain.

More particularly, the anionic amphiphilic polymers comprising at least one hydrophobic chain which are crosslinked or non-crosslinked, comprise at least one hydrophilic unit derived from one or more ethylenically unsaturated monomers bearing a carboxylic acid function, or a sulphonic function which is free or partially or totally neutralized, and at least one hydrophobic unit derived from one or more ethylenically unsaturated monomers bearing a hydrophobic side chain, and optionally at least one crosslinking unit derived from one or more polyunsaturated monomers.

The amphiphilic polymers may also comprise at least one sulphonic group, in free or partially or totally neutralized form and at least one hydrophobic portion.

Among these, mention may be made more particularly of acrylamido-2-methyl-2-propanesulphonic (AMPS) acid/n-dodecylacrylamide copolymer neutralized with sodium hydroxide, the copolymer crosslinked with methylenebisacrylamide consisting of 75% by weight of AMPS units neutralized by $NH_3$ and 25% by weight of Genapol T-250 acrylate units, the copolymer crosslinked with allyl methacrylate consisting of 90% by weight of AMPS units neutralized with $NH_3$ and 10% by weight of Genapol T-250 methacrylate units, or the copolymer crosslinked with allyl methacrylate consisting of 80% by weight of AMPS units neutralized with $NH_3$ and 20% by weight of Genapol T-250 methacrylate units.

Other examples include Carbopol ETD-2020 (acrylic acid/$C_{10}$-$C_{30}$ alkyl methacrylate crosslinked copolymer sold by the company Noveon); Carbopol 1382, Pemulen TR1 and Pemulen TR2 (acrylic acid/$C_{10}$-$C_{30}$ alkyl acrylate crosslinked copolymers—sold by the company Noveon), the methacrylic acid/ethyl acrylate/oxyethylenated stearyl methacrylate copolymer (55/35/10); the (meth)acrylic acid/ethyl acrylate/25 EO oxyethylenated behenyl methacrylate copolymer (Aculyn 28 sold by Rohm & Haas) and the methacrylic acid/ethyl acrylate/steareth-10 alkyl ether crosslinked copolymer.

When the compositions of the present invention comprise one or more amphiphilic polymer(s) containing a hydrophobic chain, then this or these polymer(s) generally represent(s) from 0.01% to 20% by weight and preferably, from 0.05% to 10% by weight of the total weight of each composition.

The rheology modifier(s) that may be present in the compositions of the present invention is (are) polymers of natural origin or synthetic polymers, and are advantageously chosen from those conventionally used in cosmetics.

Examples of synthetic polymers that may be mentioned include polyvinylpyrrolidone, polyacrylic acid, polyacrylamide, non-crosslinked poly(2-acryl-amidopropanesulphonic acid) (Simugel EG from the company SEPPIC), crosslinked poly(2-acrylamido-2-methylpropanesulphonic acid), free or partially neutralized with ammonia (Hostacerin AMPS from Clariant), mixtures of non-crosslinked poly(2-acrylamido-2-methylpropanes-ulphonic acid) with hydroxyalkylcellulose ethers or with poly(ethylene oxide)s, as described in U.S. Pat. No. 4,540,510; mixtures of poly((meth)acrylamido($C_1$-$C_4$) alkylsulphonic acid), which is preferably crosslinked, with a crosslinked copolymer of maleic anhydride and of a ($C_1$-$C_5$) alkyl vinyl ether (Hostacerin AMPS/Stabileze QM from the company ISF).

The thickening polymers of natural origin are preferably polymers comprising at least one sugar unit, for instance nonionic guar gums, optionally modified with $C_1$-$C_6$ hydroxyalkyl groups; biopolysaccharide gums of microbial origin, such as scleroglucan gum or xanthan gum; gums derived from plant exudates, such as gum arabic, ghatti gum, karaya gum, gum tragacanth, carrageenan gum, agar gum and carob gum; pectins; alginates; starches; hydroxy($C_1$-$C_6$)alkylcelluloses and carboxy($C_1$-$C_6$)alkylcelluloses.

It should be noted that the term "sugar unit" denotes a monosaccharide (i.e. monosaccharide or aside or simple sugar) portion, an oligosaccharide portion (short chains formed from a sequence of monosaccharide units, which may be different) or a polysaccharide portion [long chains consisting of monosaccharide units, which may be different, i.e. polyholosides or polyosides]. The saccharide units may also be substituted with alkyl, hydroxyalkyl, alkoxy, acyloxy or carboxyl radicals, the alkyl radicals containing from 1 to 4 carbon atoms.

Examples of nonionic, unmodified guar gums that may be mentioned, inter alia, include Guargel D/15 (Noveon); Vidogum GH 175 (Unipectine), Meypro-Guar 50 and Jaguar C (Meyhall/Rhodia Chimie); and the modified nonionic guar gums that may be mentioned include Jaguar HP8, HP60, HP120, DC 293 and HP 105 (Meyhall/Rhodia Chimie); Galactasol 4H4FD2 (Aqualon).

Among these gums, mention will be made of scleroglucans such as, especially, Actigum CS from Sanofi Bio Industries; Amigel from Alban Muller International, and also the glyoxal-treated scleroglucans described in FR 2 633 940); xanthan gums, for instance Keltrol, Keltrol T, Keltrol Tf, Keltrol Bt, Keltrol Rd, Keltrol Cg (Nutrasweet Kelco), Rhodicare S and Rhodicare H (Rhodia Chimie); starch derivatives, for instance Primogel (Avebe); hydroxyethylcelluloses such as Cellosize QP3L, QP4400H, QP30000H, HEC30000A and Polymer PCG10 (Amerchol), Natrosol 250HHR, 250MR, 250M, 250HHXR, 250HHX, 250HR, HX (Hercules) and Tylose H1000 (Hoechst); hydroxypropylcelluloses, for instance Klucel EF, H, LHF, MF and G (Aqualon); carboxymethylcelluloses, for instance Blanose 7M8/SF, refined 7M, 7LF, 7MF, 9M31F, 12M31XP, 12M31P, 9M31XF, 7H, 7M31, 7H3SXF (Aqualon), Aquasorb A500 (Hercules), Ambergum 1221 (Hercules), Cellogen HP810A, HP6HS9 (Montello) and Primellose (Avebe).

The preferred rheology-modifying agents in the present invention are also chosen from cellulose derivatives, polysaccharides, gums, clays, fumed silica, acrylates, polyacrylamides, crosslinked polyacrylic acids, crosslinked acrylamide polymers and copolymers, crosslinked methacryloyloxyethltrimethylammonium chloride homopolymers, associative polymers.

The preferred rheology-modifying agents in the present invention are chosen from xanthan gum, gum arabic, ghatti gum, karaya gum, gum tragacanth, carrageenan gum, agar gum, carob gum, pectins, alginates, starches, hydroxy($C_1$-$C_6$)alkylcelluloses, carboxy($C_1$-$C_6$)alkylcelluloses, and mixtures thereof.

In general, the at least one rheology modifying agent is present in an amount ranging from 0.1% by weight to 40% by weight, preferably from about 0.5% to about 30% by weight, more preferably from about 1% to about 20% by weight, based on the total weight of the bleach composition.

According to a preferred embodiment, the at least one rheology-modifying agent will be present in an amount of at least 1% by weight, based on the total weight of the bleach composition.

According to a preferred embodiment, the at least one rheology modifying agent is present in an amount ranging from 0.1% by weight to 30% by weight, preferably from about 0.5% to about 25% by weight, more preferably from about 1% to about 20% by weight, based on the total weight of the lightening composition formed from the combination of the bleach composition and the developer composition.

The bleach composition may be in the form of a powder, gel, liquid, foam, lotion, cream, mousse, and emulsion.

In a preferred embodiment, the bleach composition is in powder form.

In another preferred embodiment, the bleach composition is in the form of a cream.

According to another preferred embodiment of the invention, the bleach composition is anhydrous.

The term "anhydrous" means that the bleach composition is either completely free of unbound water or contains no appreciable amount of unbound water, preferably no more than 1% by weight, and more preferably no more than 0.5% by weight, based on the weight of the bleach composition.

The bleach composition of the present invention may also contain acid and alkali pH adjusters that are well known in the art in the cosmetic treatment of keratin fibers. Such pH adjusters include sodium metasilicate, silicate compounds, citric acid, ascorbic acid, and carbonate compounds. The pH adjuster is present in the bleach composition in an amount effective to provide the lightening composition with a pH ranging from 2 to 7 when the bleach composition is combined with the developer composition of the present invention.

When a pH adjuster is present in the bleach composition, the amount of pH adjuster is at least about 0.01%, preferably, at least about 0.1%, more preferably, at least about 0.2%, and even more preferably, at least about 0.5%.

According to one embodiment of the present invention, the bleach composition is acidic, with the pH ranging from about 2 to about 7.

According to another embodiment of the present invention, the bleach composition has a pH higher than 7.

When the bleach composition is in powder form, the pH may be measured in a 1% solution in water.

The bleach composition of the present invention may also contain dessicants, such as silica. The silica is preferably present in an amount of from about 1 to about 3% by weight of the dessicant, based on the total weight of the bleach composition.

The bleach composition of the present invention may also contain chelating agents, such as ethylenediamine tetraacetic acid, its salt and mixtures thereof. The chelating agent is preferably present in an amount of from about 0.01 to about 2% by weight of the chelating agent based on the total weight of the bleach composition.

De-dusting agents may also be incorporated in the bleach compositions of the present invention when the bleach composition is in powder form. The de-dusting agents include hydrophobic agents, for example, oils, esters, alkanes, alkenes, and mixtures thereof.

The de-dusting agent comprises less than 10 percent by weight based on the total weight of the bleach composition. More preferably the bleach composition comprises about 1 to about 5% and, most preferably, about 2 to about 4% de-dusting agent by weight based on the total weight of the bleach composition.

Colorants may also be present in the bleach compositions of the present invention. The colorants suitable for the invention are those colorants that are stable in the bleach composition and can impart additional toning and coloring to hair.

Suitable hair colorants include, but are not limited to, pigments, liposoluble dyes, direct dyes, nacreous pigments, pearling agents, leuco dyes, optical lightening colorants, natural colorants and optically-variable pigments. Preferably, the colorants which may be present in the compositions of the present invention are non-oxidative colorants or dyes.

Developer Composition

The developer composition of the present invention comprises hydrogen peroxide and a cosmetically acceptable carrier.

In general, hydrogen peroxide is present in an amount of at least 1% by weight, based on the total weight of the developer composition.

According to a preferred embodiment, hydrogen peroxide is present in an amount ranging from 1% by weight to 80% by weight, preferably from about 1.5% to about 75% by weight, more preferably from about 2% to about 10% by weight, based on the total weight of the developer composition.

The developer composition of the present invention contains a cosmetically acceptable carrier chosen from water, organic solvents, natural oils, synthetic oils, esters, hydrocarbons, silicones and mixtures thereof.

A suitable cosmetically acceptable carrier includes alcohols, such as ethanol, isopropyl alcohol, benzyl alcohol and phenyl ethyl alcohol; glycols and glycol ethers, such as propylene glycol, hexylene glycol, ethylene glycol monomethyl, monoethyl or monobutyl ether, propylene glycol and its ethers, such as propylene glycol monomethyl ether, butylene glycol, dipropylene glycol, and also diethylene glycol alkyl ethers, such as diethylene glycol monoethyl ether and monobutyl ether; hydrocarbons such as straight chain hydrocarbons, mineral oil, polybutene, hydrogenated polyisobutene, hydrogenated polydecene, polydecene, squalene, petrolatum and isoparaffins; and mixtures, thereof.

The cosmetically acceptable carrier may, for example, be present in an amount ranging from 0.5% to 99% by weight, preferably from 5 to 95% by weight, relative to the total weight of the developer composition.

The pH of the developer composition can range from 2 to 5, such as from 2 to 4, and it may be adjusted to the desired value using pH adjusters that are well known in the art in the cosmetic treatment of keratin fibers.

The developer composition may be in the form of a powder, gel, liquid, foam, lotion, cream, mousse, and emulsion.

In one embodiment, the developer composition is in powder form.

In one preferred embodiment, the developer composition is in the form of a liquid.

In another preferred embodiment, the developer composition is in the form of a lotion.

In another preferred embodiment, the developer composition is in the form of a lotion.

According to one embodiment of the invention, the developer composition is anhydrous.

The term "anhydrous" means that the developer composition is either completely free of unbound water or contains no appreciable amount of unbound water, preferably no more than 1% by weight, and more preferably no more than 0.5% by weight, based on the weight of the developer composition.

Surfactant-Based Composition

A surfactant-based composition may also be applied onto the hair after the hair is treated with the lightening composition of the present invention. The surfactant-based composition may contain at least one surfactant, chosen from anionic, amphoteric, non-ionic, zwitterionic, cationic surfactants, and mixtures thereof.

The surfactant-based composition of the present invention is also comprised of any suitable solvents chosen from water, organic solvents, silicones and mixtures thereof. Such a composition containing at least one surfactant chosen from anionic, amphoteric, nonionic, zwitterionic, cationic surfactants, and mixtures thereof.

The surfactant-based composition of the present invention may be in the form of a shampoo, a rinse conditioner, non-rinse conditioner or leave-on treatment composition.

The at least one surfactant in the surfactant-based composition of the present invention may be present in an amount ranging from 0.01% to 40%, such as from 0.05% to 30%, relative to the total weight of the surfactant-based composition of the present invention.

Additional Ingredients

The described embodiments of the present invention may also include one or more additional ingredients, which may be incorporated into the bleach composition, the developer composition, and surfactant-based composition. Such ingredients include well-known conventional additives typically employed in hair cosmetic compositions such as acidifying agents, buffering agents, rheological modifiers, conditioning agents, surfactants, antioxidants, fragrances, and chelating agents.

A. Conditioning Agents

The compositions of the present invention may also contain at least one conditioning agent. Such conditioning agents are typically chosen from synthetic oils such as polyolefins, plant oils, fluoro oils or perfluoro oils, natural or synthetic waxes, silicones, non-polysaccharide cationic polymers, compounds of ceramide type, cationic surfactants, fatty amines, fatty acids and derivatives thereof, and also mixtures of these various compounds. Other useful conditioning agents are conditioning polymers which contain primary, secondary, tertiary and/or quaternary amine groups, forming part of the polymer chain or linked directly to the latter, and having a molecular weight of between 500 and approximately 5,000,000, and preferably between 1000 and 3,000,000.

Among these polymers, there may be mentioned, more especially, quaternized proteins, polymers of the polyamine, polyaminoamide or poly(quaternary ammonium) family and cationic polysiloxanes.

The quaternized proteins are, in particular, chemically modified polypeptides bearing quaternary ammonium groups at the end of the chain or grafted onto the latter.

Among the polyamine, polyaminoamide or poly(quaternary ammonium) family of polymers, there may be mentioned:

1) Vinylpyrrolidone/dialkylaminoalkyl acrylate or methacrylate copolymers, quaternized or otherwise, such as the products sold by the company GAF CORPORATION under the name "GAFQUAT", for example "GAFQUAT 734 or 755", or alternatively the products designated "COPOLYMER 845, 958 and 937".

2) The cellulose ether derivatives containing quaternary ammonium groups, especially the polymers marketed by the company UNION CARBIDE CORPORATION under the names "JR" (JR 400, JR 125, JR 30M) or "LR" (LR 400, LR 30M). The polymers are also defined in the CTFA Dictionary as quaternary ammonium derivatives of hydroxyethylcellulose subjected to reaction with an epoxide substituted with a trimethylammonium group.

3) Cationic cellulose derivatives such as cellulose copolymers or cellulose derivatives grafted with a water-soluble quaternary ammonium monomer such as, for example hydroxyalkylcelluloses such as hydroxymethyl-, hydroxyethyl- or hydroxypropylcellulose grafted with a methacryloylethyltrimethylammonium, methacrylamidopropyltrimethylammonium or dimethyldiallylammonium salt.

Marketed products corresponding to this definition are, more especially, the products sold by the company NATIONAL STARCH under the names "CELQUAT L 200" and "CELQUAT H 100".

4) The quaternized polysaccharides marketed under the name "JAGUAR C 13 S", sold by the company MEYHALL.

5) yclopolymers having a molecular weight of 20,000 to 3,000,000 such as, for example, the homopolymer of dimethyldiallylammonium chloride sold by the company MERCK under the name "MERQUAT 100", having a molecular weight of less than 100,000, and the copolymer of dimethyldiallylammonium chloride and acrylamide having a molecular weight above 500,000 and sold under the name "MERQUAT 550".

6) Quaternary polymers of vinylpyrrolidone and of vinylimidazole, such as, for example, the products marketed by the company BASF under the names "LUVIQUAT FC 905, FC 550 and FC 370".

Other conditioning polymers which are useable according to the invention are polyalkylenimines, especially polyethylenimines, polymers containing vinylpyridine or vinylpyridinium units, condensates of polyamines and epichlorohydrin, quaternary polyureylenes and chitin derivatives.

The cationic polysiloxanes such as those described in U.S. Pat. No. 4,185,087.

The conditioning polymers may also be chosen from amphoteric polymers, such as amphoteric polymers derived from chitosan or copolymers of diallyldialkylammonium and an anionic monomer.

Preferred polymers are, inter alfa, polymers containing alkyl groups chosen from groups having 1 to 4 carbon atoms, and more especially methyl and ethyl groups.

Especially preferred conditioning polymers according to the invention are chosen from:

a) the poly(quaternary ammonium) polymers;

b) the copolymer of the diallyldimethylammonium chloride and acrylic acid (80/20) sold by the company CALGON under the name MERQUAT 280;

c) the homopolymer of dimethyldiallylammonium chloride sold by the company MERCK under the name MERQUAT 100;

d) the quaternized cellulose ether derivatives sold by the company UNION CARBIDE under the name JR;

e) the copolymer of vinylpyrrolidone and methacrylamidopropyltrimethylammonium chloride (85:15) sold by the company GAF under the name GAFQUAT HS100;

f) the polymeric quaternary ammonium salt of acrylamide and beta-methacrylyloxyethyl trimethyl ammonium methosulfate, sold by the company, Nalco, under the names polyquaternium-5 or quaternium-39 or Merquat 5; and g) the cationic polymers of the ionene type sold by the company Chimex, such as hexadimethrine chloride, also known as IONENE G.

According to a preferred embodiment, the bleach composition and/or developer composition and/or surfactant-based composition of the present invention contain at least one conditioning agent as defined above. More preferably, the bleach composition and/or developer composition and/or surfactant-based composition of the present invention contain at least one conditioning polymer, in an amount of from 0.01% to 12% by weight, preferably from 0.1 to 10% by weight, more preferably from 0.1 to 8% by weight, all weights being based on the total weight of the corresponding composition.

B. Chelating Agents

The compositions of the present invention may also contain at least one chelating agent. Preferred ranges of chelating agent are from 0.001% to 5%, preferably from 0.005% to 4%, more preferably from 0.01 to 3% by weight of each composition. Preferred chelating agents are EDTA, HEDTA, and sodium or potassium salts, and mixtures, thereof.

C. Antioxidants

The compositions of the present invention may also contain at least one antioxidant such as ascorbic acid, ascorbylated compounds, such as ascorbyl dipalmitate, t-butylhydroquinone, polyphenols, such as phloroglucinol, thiols, for example, cysteine, sodium sulfite, and sodium hydrosulfite, erythorbic acid, flavonoids, and mixtures thereof.

The antioxidant may be present in an amount ranging from 0.1% to 20% by weight relative to the total weight of the compositions of the present invention.

Other Ingredients

The compositions of the present invention can also comprise any additive typically used in cosmetic or hair treatment compositions. The additives may include waxes, organogelators, dispersants, oils, preserving agents, fragrances, fillers, neutralizing agents, hydroxy acids, UV filters, ceramides, pseudoceramides, vegetable, mineral oils, synthetic oils, vitamins, and provitamins.

Needless to say, a person skilled in the art will take care to select the optional additional compound(s) mentioned above such that the advantageous properties intrinsically associated with the compositions of the present invention disclosed herein are not, or are not substantially, adversely affected by the envisaged addition(s).

Compositions Used to Form Straightened or Relaxed Hair

There are generally two types of compositions to form straightened or relaxed hair. The first type or class is based on a whether the composition is a "lye" or "no lye" formulation. Both lye and no lye formulations employ a hydroxide compound as the active ingredient and are alkaline in nature. The "lye" based compositions contain the active ingredient, sodium hydroxide. The "no lye" compositions contain an active ingredient having a different positive cation with hydroxide, examples of which are calcium hydroxide, lithium hydroxide, potassium hydroxide, barium hydroxide and strontium hydroxide or oxides thereof capable of forming hydroxides in water. A relatively strong organic base, such as guanidine, guanidine hydroxide (generally prepared in situ from guanidine carbonate and calcium hydroxide) or quaternary ammonium hydroxide, may also be used. These compositions are commonly used in the commercially available hair straighteners bought for home use.

The second class of straightening and relaxing compositions are non-hydroxide based compositions. Examples of the second class are ammonium thioglycolate based, often referred to as "thio" straighteners or "perms". These compositions are also alkaline and are most commonly used by professional beauticians and were originally developed from the permanent wave.

Other examples of non-hydroxide based compositions employ weak organic bases and weak inorganic bases. Weak organic bases useful in straightening and relaxing compositions include nitrogen-containing bases, which do not completely disassociate in water. Examples thereof include, but are not limited to, amines such as ethylamines, ethyleneamines, ethanolamines, including cyclic amines such as for example aniline, quinoline and other cyclic compounds, saturated or unsaturated, having one or more nitrogen atoms within the ring.

Examples of five-membered rings having one nitrogen atom include, but are not limited to, pyrroline, pyrrole, pyrrolidine, and derivatives thereof.

Examples of five-membered rings having two nitrogen atoms include, but are not limited to, pyrazole, pyrazoline, imidazolidine, imidazole, imidazoline, and derivatives thereof.

Examples of six-membered rings having one nitrogen atom include, but are not limited to, morpholine, pyridine, piperidine, and derivatives thereof.

Examples of six-membered rings having two nitrogen atoms include, but are not limited to, pyridazine, pyrimidine, pyrazine, piperazine, and derivates thereof.

Examples of six-membered rings having three nitrogen atoms include, but are not limited to, triazine, and derivatives thereof.

Particularly preferred weak organic bases include ethylenediamines, monoethanolamines, imidazole, pyrrole, pyrrolidine, and mixtures thereof.

Also preferred are mixtures of the above mentioned weak organic bases, such as a mixture of ethylenediamine and imidazole, or a mixture of monoethanolamine and imidazole.

Weak inorganic bases useful in the present invention include alkali metal phosphates and carbonates such as, for example, sodium phosphate, potassium phosphate, sodium carbonate, sodium bicarbonate, potassium carbonate, potassium bicarbonate, and their derivatives.

Weak inorganic bases may also include alkali metals of carboxylates such as, for example, sodium acetate, potassium acetate, sodium citrate, and potassium citrate, and their derivatives.

Particularly preferred weak inorganic bases include potassium phosphate, sodium phosphate, and sodium carbonate.

Compositions for straightening or relaxing hair have a pH of from about 8.0 to about 14.00. Such compositions may also be called straightening or relaxing compositions.

Compositions for straightening or relaxing hair may be, for example, in the form of a thickened cream so as to hold the hair as stiff as possible. These creams are made in the form of "heavy" emulsions, for example, based on glyceryl stearate, glycol stearate, self-emulsifying waxes, fatty alcohols, mineral oil and petrolatum.

Liquids or gels containing thickeners, such as carboxyvinyl polymers or copolymers that "stick" the hair together and hold them in a smooth position during the leave-in time, may also be used.

In the event that surfactants are employed, said hair straightening/relaxing composition may be used as a shampoo. Similarly, in the event that one were to decide to use said hair straightening/relaxing composition as a hair conditioner, various types of conditioning agents can be added to the composition in order to facilitate this hair treating property.

Smoothing or straightening of hair according to the present invention may involve using a combination of heat and/or means for physically smoothing the hair. The precise amount of heat employed will depend on the concentration of the weak non-hydroxide base present in the composition. This heat may emanate from any suitable source such as, for example, a hair dryer or hot/flat iron.

The means for physically smoothing hair can be any apparatus capable of physically smoothing the hair such as, for example, a hair brush or comb. The means for smoothing hair also serves as the source for generating heat such as, for example, a hot/flat iron.

An additional embodiment of the present invention provides for using a pre-alkalizing composition on the hair before applying a straightening or relaxing composition onto the hair. By first pre-alkalizing the hair, followed by treating it with a weak non-hydroxide base composition, and smoothing the hair by employing a combination of heat and means for physically smoothing the hair, satisfactory straightening/relaxing of the hair can be achieved in a manner that is less harmful to both skin and hair.

The pre-alkalizing step can use an alkaline composition having a pH ranging from 8.0 to 10.5, preferably from 8.5 to 9.5. Any conventional base, whether alkaline hydroxide or non-hydroxide, may be employed so long as it results in the formation of an alkaline composition having the above-disclosed pH range. The precise amount of conventional base used will depend on the specific base(s) chosen. Once the hair has been pre-alkalized, the alkaline composition may, optionally, be rinsed-off before applying the straightening or relaxing composition to the hair.

The purpose of the pre-alkalizing step is to open the hair cuticle, thereby rendering it more susceptible to the subsequent penetration of the non-hydroxide base. This in turn renders the hair straightening/relaxing process more efficient and less time-consuming.

The alkaline composition may be employed in any suitable form. Examples thereof include, but are not limited to, an alkaline shampoo, an alkaline conditioner or an alkaline solution in general. In a particularly preferred embodiment, the alkaline composition is in the form of an alkaline shampoo which would facilitate both the pre-alkalizing and cleaning of the hair at the same time.

The lightening composition of the present invention is applied onto the hair within 24 hours after straightening or relaxing the hair with a straightening or relaxing composition. The hair being straightened or relaxed may be dry, damp or wet.

In one preferred embodiment, the lightening composition of the present invention is applied onto the hair within a few minutes after the process of straightening or relaxing the hair with a straightening or relaxing composition.

In another preferred embodiment, the lightening composition of the present invention is applied onto the hair immediately after the process of straightening or relaxing the hair with a straightening or relaxing composition.

The lightening composition of the present invention is applied onto the hair to simultaneously lighten the color of the hair and neutralize any excess relaxing or straightening composition on the hair In one preferred embodiment, the bleach composition is mixed with the developer composition to form the lightening composition right before applying the lightening composition onto the hair. The lightening composition is left on the hair for a period of time sufficient to lighten the hair for a period of from 1 to 30 minutes, such as from 1 to 10 minutes, for example from 1 to 5 minutes.

The pH of the mixture formed from the combination of the bleach composition and the developer composition preferably ranges from between about 2 to about 7, more preferably from between about 2.5 to about 6.5, and even more preferably from between about 3 to about 6

In one preferred embodiment, the bleach composition and developer composition are combined to form the lightening composition in a ratio of bleach composition to developer composition ranging from about 1:1 to about 1:5, preferably from about 1:2 to about 1:4.

In one preferred embodiment, the at least one oxidizing agent in the lightening composition is present in an amount ranging from 5% by weight to 50% by weight, preferably from about 10% to about 30% by weight, more preferably from about 15% to about 25% by weight, based on the total weight of the lightening composition.

In another preferred embodiment, hydrogen peroxide in the lightening composition is present in an amount ranging from 0.1% by weight to 50% by weight, preferably from about 0.5% to about 25% by weight, more preferably from about 1% to about 10% by weight, based on the total weight of the lightening composition.

As used herein, the method and composition disclosed herein may be used on the hair that has not been artificially dyed or pigmented.

As used herein, the method and composition disclosed herein may be also used on the hair that has been artificially dyed or pigmented.

The lightening of the hair is, evaluated by the tone height or level which describes the degree or level of lightening. The notion of "tone" is based on the classification of the natural shades, one tome separating each shade from the shade immediately following or preceding it. This definition is well known to hairstyling professionals. The tone heights range from 1 (black) to 10 (light blond), one unit corresponding to one tone; the higher the number, the lighter the shade.

The present invention will be better understood from the examples which follow, all of which are intended to illustrate the invention, and are not meant to unduly limit the scope of the invention in any way.

EXAMPLES

Compositions

Example 1

Inventive Composition

Bleach Composition:

| Ingredient | Wt % |
| --- | --- |
| POTASSIUM PERSULFATE | 45.00 |
| SODIUM PERSULFATE | 20.00 |
| EDTA | 0.70 |
| SILICA | 1.00 |
| XANTHAN GUM | 6.00 |
| POLYDECENE | 1.70 |
| pH ADJUSTER | 0.20% |
| CORN STARCH | Q.S. to 100.0 |

Developer Composition:

| Ingredient | Wt % |
| --- | --- |
| CETEARYL ALCOHOL (and) CETEARETH-25 | 2.85 |
| TRIDECETH-2 CARBOXAMIDE MEA | 0.85 |
| GLYCERINE | 0.50 |
| TETRASODIUM PYROPHOSPHATE | 0.02 |
| SODIUM STANNATE | 0.04 |
| PENTASODIUM PENTETATE | 0.15 |
| HYDROGEN PEROXIDE | 4.00 |
| DEIONIZED WATER | Q.S. to 100.0 |

Example 2

Comparative

Bleach Composition (Alkaline pH):

| Ingredient | Wt % |
| --- | --- |
| POTASSIUM PERSULFATE | 36.00 |
| SODIUM PERSULFATE | 11.50 |
| SODIUM SILICATE | 24.00 |
| AMMONIUM SULFATE | 5.00 |
| SODIUM METASILICATE | 2.00 |
| CORN STARCH | 6.25 |
| SODIUM LAURYL SULFATE | 4.00 |
| XANTHAN GUM | 2.50 |
| SODIUM STEARATE | 2.00 |
| HYDRATED SILICA | 1.75 |
| ACRYLATES/C10-30 ALKYL ACRYLATE CROSSPOLYMER | 1.00 |
| FRAGRANCE | 1.00 |
| PANTHENOL | 0.50 |
| EDTA | 0.25 |
| ULTRAMARINES | 0.25 |
| POLYDECENE | 2.00 |

Developer Composition:

| Ingredient | Wt % |
| --- | --- |
| CETEARYL ALCOHOL (and) CETEARETH-25 | 2.85 |
| TRIDECETH-2 CARBOXAMIDE MEA | 0.85 |
| GLYCERINE | 0.50 |
| TETRASODIUM PYROPHOSPHATE | 0.02 |
| SODIUM STANNATE | 0.04 |
| PENTASODIUM PENTETATE | 0.15 |
| HYDROGEN PEROXIDE | 4.00 |
| DEIONIZED WATER | Q.S. to 100.0 |

Procedure:

Dark Brown (level 3) hair was relaxed using a traditional lye relaxer and processed according to the directions for 15 minutes. The hair was then rinsed with water. The lightening composition of Example 1 was formed by mixing 13 grams of the bleach composition+30 grams of the developer composition and applied to the relaxed hair. This mixture was left on the hair for 30 minutes, and then rinsed with water and dried.

Similarly, the composition of Example 2 was formed by mixing 13 grams of the alkaline bleach composition with 30 grams of the developer composition and applied to the relaxed hair. This mixture was left on the hair for 5 minutes (only 5 minutes to obtain equal degree of lift as in Example 1 above), and then rinsed with water and dried.

pH Determination: The treated hair was soaked in 250 mL deionized water for 5 minutes. The pH of the water was then measured in order to determine the pH of the lightening composition formed by combining the bleach composition and the developer composition.

Results:

|  | Hair pH |
| --- | --- |
| Virgin Hair | 6.69 |
| Relaxed Hair (no neutralizing shampoo) | 10.84 |
| Hair lightened with Example 1 (invention) | 3.68 |
| Hair lightened with Example 2 | 9.59 |

The results above show that the lightening composition was acidic, having a pH of 3.68, compared to the pH of the other compositions.

Colorimetric study: The lightness of the color of the treated hair was measured by colorimetric measurements using a Minolta CM2002 colorimeter in the L*a*b* system. According to this system, the greater the value of L, the lighter or less intense the color. Conversely, the lower the value of L, the darker or more intense the color.

Results:

|  | L-Value |
| --- | --- |
| Untreated Level 3 hair | 24.24 |
| Level 3 + Lightening Composition | 25.57 |
| Level 3 + Relaxer + Lightening Composition | 30.15 |

The results above show that the use of the acidic lightening composition on relaxed hair yielded a greater increase in lightness of the color of the hair compared to the use of the acidic lightening composition on hair that was not relaxed prior to the use of the lightening composition.

It is to be understood that the foregoing describes preferred embodiments of the invention and that modifications may be made therein without departing from the spirit or scope of the invention as set forth in the claims.

The invention claimed is:

1. A method of lightening the color of hair that has been recently contacted with a relaxing or straightening composition, the method comprising:
   (a) combining a bleach composition comprising at least one oxidizing agent selected from the group consisting of persulfates, perborates, percarbonates, their salts and mixtures thereof; and at least one rheology-modifying agent, with a developer composition comprising hydrogen peroxide and a cosmetically acceptable carrier in order to form a lightening composition, wherein the pH of the lightening composition is from about 2 to about 7;
   (b) applying the lightening composition onto hair that has been recently contacted with a relaxing or straightening composition;
   (c) leaving the lightening composition on the hair for a time period sufficient to achieve an increase of 1 to 4 in the tone height of the hair; and
   (d) optionally, rinsing the hair.

2. The method of claim 1 wherein the at least one oxidizing agent of the bleach composition in (a) is present in an amount of at least 40% by weight, based on the total weight of the bleach composition.

3. The method of claim 1 wherein the at least one oxidizing agent of the bleach composition in (a) is present in an amount of from about 40% to about 75% on the total weight of the bleach composition.

4. The method of claim 1 wherein the at least one rheology-modifying agent of the bleach composition in (a) is selected from the group consisting of cellulose derivatives, polysaccharides, gums, clays, fumed silica, acrylates, polyacrylamides, crosslinked polyacrylic acids, crosslinked acrylamide polymers and copolymers, crosslinked methacryloyloxyethltrimethylammonium chloride homopolymers, associative polymers and mixtures thereof.

5. The method of claim 1 wherein the at least one rheology-modifying agent of the bleach composition in (a) is present in an amount ranging from about 0.1% to about 40% based on the total weight of the bleach composition.

6. The method of claim 1 wherein the at least one rheology-modifying agent of the bleach composition in (a) is present in an amount ranging from about 1% to about 20% based on the total weight of the bleach composition.

7. The method of claim 1 wherein the bleach composition further comprises a cosmetically acceptable carrier.

8. The method of claim 1 wherein the bleach composition in (a) further comprises at least one additive ingredient.

9. The method of claim 8 wherein the at least one additive ingredient is silica.

10. The method of claim 8 wherein the at least one additive ingredient is a de-dusting agent.

11. The method of claim 1 wherein hydrogen peroxide in the developer composition in (a) is present in an amount ranging from about 0.5 to about 20% based on the total weight of the developer composition.

12. The method of claim 1 wherein the cosmetically acceptable carrier of the developer composition in (a) is selected from the group consisting of water, organic solvents, natural oils, synthetic oils, esters, hydrocarbons, silicones and mixtures thereof.

13. The method of claim 1 wherein the developer composition in (a) further comprises at least one additive ingredient.

14. The method of claim 1 further comprising contacting the hair with a surfactant-based composition.

15. The method of claim 14 further comprising rinsing the hair contacted with the surfactant-based composition.

16. The method of claim 14 wherein the surfactant-based composition comprises at least one surfactant selected from the group consisting of anionic surfactants, amphoteric surfactants, non-ionic surfactants, zwitterionic surfactants, cationic surfactants, and mixtures thereof.

17. The method of claim 1 wherein combining the bleach composition and the developer composition includes combining the bleach composition with the developer composition in a ratio of from about 1:1 to about 1:5.

18. The method of claim 1 wherein the bleach composition further comprises a pH adjuster.

19. A composition for lightening the color of hair that has been recently contacted with a relaxing or straightening composition, the composition comprising:
   (a) a bleach composition containing:
      i. at least one oxidizing agent selected from the group consisting of persulfates, perborates, percarbonates, their salts and mixtures thereof; and
      ii. at least one rheology-modifying agent; and
   (b) a developer composition containing:
      i. hydrogen peroxide; and
      ii. a cosmetically acceptable carrier; and
   wherein the lightening composition has a pH of about 2 to about 7.

* * * * *